US006507633B1

(12) United States Patent
Elbakri et al.

(10) Patent No.: US 6,507,633 B1
(45) Date of Patent: Jan. 14, 2003

(54) METHOD FOR STATISTICALLY RECONSTRUCTING A POLYENERGETIC X-RAY COMPUTED TOMOGRAPHY IMAGE AND IMAGE RECONSTRUCTOR APPARATUS UTILIZING THE METHOD

(75) Inventors: Idris A. Elbakri, Ann Arbor, MI (US); Jeffrey A. Fessler, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 143 days.

(21) Appl. No.: 09/784,740

(22) Filed: Feb. 15, 2001

(51) Int. Cl.$^7$ .................................................. A61B 6/03
(52) U.S. Cl. ....................... 378/8; 378/4; 378/5; 378/94
(58) Field of Search ............................... 378/4, 5, 8, 9, 378/94

(56) References Cited

U.S. PATENT DOCUMENTS

| 4,247,774 A | * | 1/1981 | Brooks ........................ 417/217 |
| 4,686,695 A | | 8/1987 | Macovski |
| 5,438,602 A | | 8/1995 | Crawford et al. |
| 5,953,444 A | | 9/1999 | Joseph et al. |

OTHER PUBLICATIONS

Chye Hwang Yan et al: "Reconstuction algorithm ford polychromatic CT imaging: application to beam hardening correction" IEEE Transactions on Medical Imaging, Jan. 2000, IEEE, USA, vol. 19, No. 1, pp. 1–11, XP002180095, ISSN: 0278–0062 cited in the application abstract section III.

Erdogan H et al: "Ordered subsets algorithms for transmission tomography" Physics in Medicine and Biology, Nov. 1999, IOP Publishing, UK, vol. 44, No. 11, pp. 2835–2851, XP001032919, ISSN: 0031–9155, abstract.
Erdogan H et al: "Monotonic algorithms for transmission tomography" IEEE Transactions on Medical Imaging, Sep. 1999, IEEE, USA, vol. 18, No. 9, pp. 801–814, XP002180097; ISSN: 0278–0062, abstract.
Joseph P M et al: "A method for simultaneous correction of spectrum hardening artifacts in CT images containing bone and iodine" Medical Physics, Oct. 1997, AIP for American Assoc. Phys. Med, USA, vol. 24, No. 10, pp. 1629–1634 XP002180098, ISSN: 0094–2405, abstract.

* cited by examiner

*Primary Examiner*—David V. Bruce
(74) *Attorney, Agent, or Firm*—Brooks & Kushman P.C.

(57) ABSTRACT

A method for statistically reconstructing an X-ray computed tomography image produced by a single X-ray CT scan having a polyenergetic source spectrum and an image reconstructor which utilize a convergent statistical algorithm which explicitly accounts for the polyenergetic source spectrum are provided. First and second related statistical iterative methods for CT reconstruction based on a Poisson statistical model are described. Both methods are accelerated by the use of ordered subsets, which replace sums over the angular index of a sinogram with a series of sums over angular subsets of the sinogram. The first method is generalized to model the more realistic case of polyenergetic computed tomography (CT). The second method eliminates beam hardening artifacts seen when filtered back projection (FBP) is used without post-processing correction. The methods are superior to FBP reconstruction in terms of noise reduction. The method and image reconstructor of the invention are effective in producing corrected images that do not suffer from beam hardening effects.

20 Claims, 5 Drawing Sheets

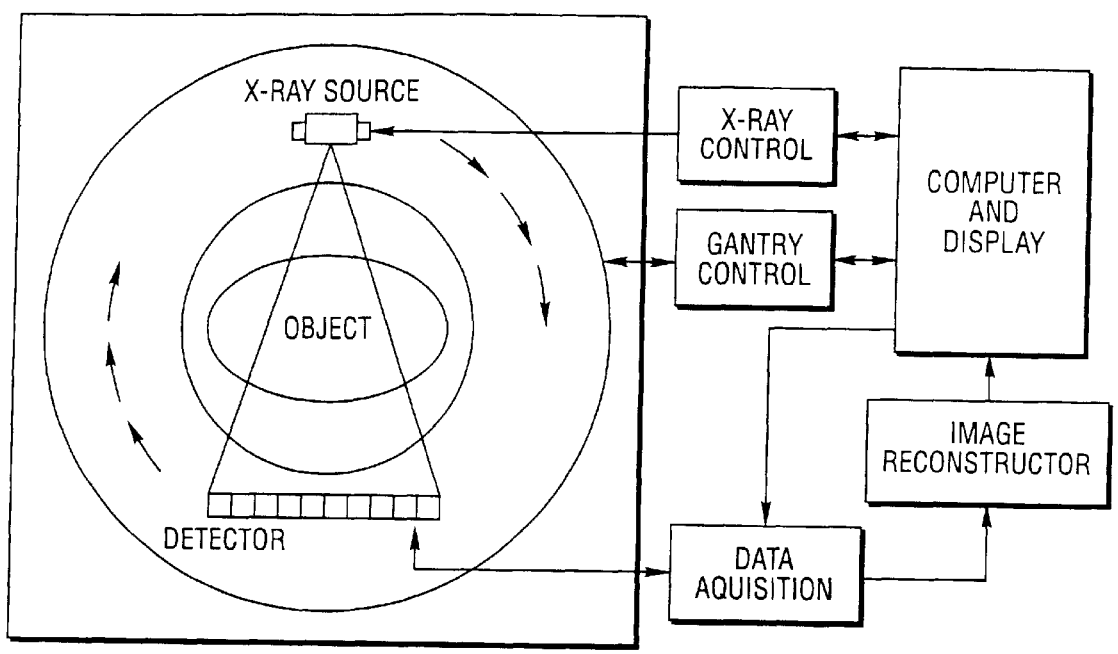
Fig. 1
*(PRIOR ART)*
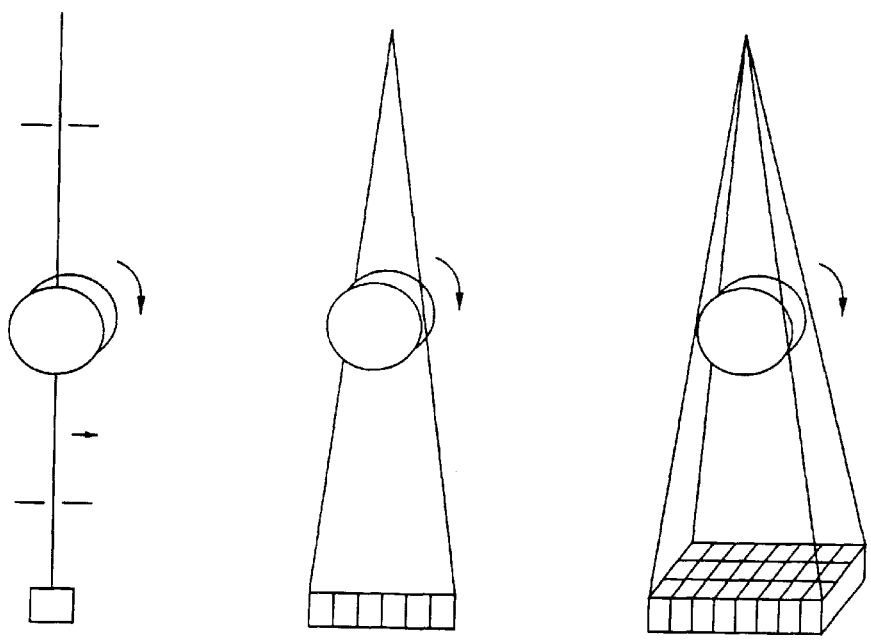
Fig. 2a
*(PRIOR ART)*
Fig. 2b
*(PRIOR ART)*
Fig. 2c
*(PRIOR ART)*

METHOD FOR STATISTICALLY RECONSTRUCTING A POLYENERGETIC X-RAY COMPUTED TOMOGRAPHY IMAGE AND IMAGE RECONSTRUCTOR APPARATUS UTILIZING THE METHOD

GOVERNMENT RIGHTS

This invention was made with government support under NIH Grant No. RO1CA/CA60711. The government has certain rights in the invention.

BACKGROUND OF THE INVENTION

1. Field of the Invention

The present invention relates to statistical methods for reconstructing a polyenergetic X-ray computed tomography image and image reconstructor apparatus and, in particular, to methods and reconstructor apparatus which reconstruct such images from a single X-ray CT scan having a polyenergetic source spectrum.

2. Background Art

X-ray computed or computerized tomography (i.e. CT) provides structural information about tissue anatomy. Its strength lies in the fact that it can provide "slice" images, taken through a three-dimensional volume with enhanced contrast and reduced structure noise relative to projection radiography.

FIG. 1 illustrates a simple CT system. An X-ray source is collimated and its rays are scanned through the plane of interest. The intensity of the X-ray photons is diminished by tissue attenuation. A detector measures the photon flux that emerges from the object. This procedure is repeated at sufficiently close angular samples over 180° or 360°. The data from different projections are organized with the projection angles on one axis and the projection bins (radial distance) on the other. This array is referred to as the sinogram, because the sinogram of a single point traces a sinusoidal wave. Reconstruction techniques have the goal of estimating the attenuation map of the object that gave rise to the measured sinogram.

FIGS. 2a–2c illustrate the evolution of CT geometries. FIG. 2a is a parallel-beam (single ray) arrangement, much like what was found in a first-generation CT scanner. The major drawback of this arrangement is long scan time, since the source detector arrangement has to be translated and rotated.

The fan-beam geometry of FIG. 2b reduces the scan time to a fraction of a second by eliminating the need for translation. By translating the patient table as the source detector arrangement rotates, one gets an effective helical path around the object leading to increased exposure volume and three-dimensional imaging.

The latest CT geometry is the cone-beam arrangement, shown in FIG. 2c. It further reduces scan time by providing three-dimensional information in one rotation. It is most efficient in its usage of the X-ray tube, but it suffers from high scatter ($\geq 40\%$). It is also the most challenging in terms of reconstruction algorithm implementation.

Two dominant effects, both a function of the X-ray source spectrum, govern tissue attenuation. At the lower energies of interest in the diagnostic region, the photoelectric effect dominates. At higher energies, Compton scattering is the most significant source of tissue attenuation.

The linear attenuation coefficient $\mu(x,y,z,E)$ characterizes the overall attenuation property of tissue. It depends on the spatial coordinates and the beam energy, and has units of inverse distance. For a ray of infinitesimal width, the mean photon flux detected along a particular projection line $L_i$ is given by:

$$E[Y_i] = \int I_i(E) e^{-\int_{L_i} \mu(x,y,z,E) dl} dE \qquad (1)$$

where the integral in the exponent is taken over the line $L_i$ and $I_i(E)$ incorporates the energy dependence of the incident ray and detector sensitivity. The goal of any CT algorithm is to reconstruct the attenuation map $\mu$ from the measured data $[Y_1, \ldots, Y_N]$ where N is the number of rays measured.

Filtered Back Projection

Filtered back projection (FBP) is the standard reconstruction technique for X-ray CT. It is an analytic technique based on the Fourier slice theorem.

Use of the FFT in the filtering step of FBP renders the algorithm quite fast. Moreover, its properties are well understood. However, because it ignores the noise statistics of the data, it results in biased estimators. It also suffers from streak artifacts when imaging objects with metallic implants or other high-density structures.

Polyenergetic X-ray CT

In reality, the attenuation coefficient $\mu$ is energy dependent and the X-ray beam is polyenergetic. Lower energy X-rays are preferentially attenuated. FIG. 7 shows the energy dependence of the attenuation coefficients of water (density 1.0 gm/cm$^3$) and bone (at density 1.92 gm/cm$^3$). A hard X-ray beam is one with higher average energy. Beam hardening is a process whereby the average energy of the X-ray beam increases as the beam propagates through a material. This increase in average energy is a direct consequence of the energy dependence of the attenuation coefficient.

With a polyenergetic source, the expected detected photon flux along path $L_i$ is given by (1). If one were to ignore the energy dependence of the measurements and simply apply FBP to the log processed data, some attenuation map $\mu$ would be reconstructed that is indirectly related to the source spectrum and object attenuation properties.

Beam hardening leads to several disturbing artifacts in image reconstruction. FIGS. 8 and 9 show the effect of beam hardening on the line integral in bone and water. In the monoenergetic case, the line integral increases linearly with thickness. With a polyenergetic beam, the soft tissue line integral departs slightly from the linear behavior. The effect is more pronounced for high Z (atomic number) tissue such as bone.

This non-linear behavior generally leads to a reduction in the attenuation coefficient. In bone, beam hardening can cause reductions of up to 10%. Thick bones also generate dark streaks. In soft tissue, the values are depressed in a non-uniform manner, leading to what has been termed the "cupping" effect. In addition, bone areas can "spill over" into soft tissue, leading to a perceived increase in the attenuation coefficient.

Beam Hardening Correction Methods

Because of SNR considerations, monoenergetic X-ray scanning is not practical. Beam hardening correction methods are therefore necessary for reconstructing artifact-free attenuation coefficient images. An ideal reconstruction method would be quantitatively accurate and portable to different scanning geometries. It would somehow reconstruct $\mu(x,y,E)$, retaining the energy dependence of the attenuation process. This is difficult, if not impossible, to achieve with a single source spectrum. A more realistic goal is to remove or reduce the beam hardening artifacts by compensating for the energy dependence in the data.

There are a wide variety of schemes for beam hardening artifact reduction. Existing methods fall into three categories: dual-energy imaging, preprocessing of projection data and post-processing of the reconstructed image.

Dual-energy imaging has been described as the most theoretically elegant approach to eliminate beam hardening artifacts. The approach is based on expressing the spectral dependence of the attenuation coefficient as a linear combination of two basis function, scaled by constants independent of energy. The two basis functions are intended to model the photo-electric effect and Compton scattering. This technique provides complete energy dependence information for CT imaging. An attenuation coefficient image can, in principle, be presented at any energy, free from beam hardening artifacts. The method's major drawback is the requirement for two independent energy measurements. This has inhibited its use in clinical applications, despite the potential diagnostic benefit of energy information. Recently, some work has been presented on the use of multi-energy X-ray CT for imaging small animals. For that particular application, the CT scanner was custom built with an energy-selective detector arrangement.

Commercial beam hardening correction methods usually involve both pre-processing and post-processing, and are often implemented with a parallel or fan-beam geometry in mind. They also make the assumption that the object consists of soft tissue (water-like) and bone (high Z). Recently, these methods were generalized to three base materials and cone-beam geometry.

Pre-processing works well when the object consists of homogeneous soft tissue. Artifacts caused by high Z materials such as bone mandate the use of post-processing techniques to produce acceptable images.

The attenuation coefficient of some material k is modeled as the product of the energy-dependent mass attenuation coefficient $m_k(E)$ (cm$^2$/g) and the energy-independent density $\rho(x,y)$ (g/cm$^3$) of the tissue. Expressed mathematically, $$\mu(x, y, E) = \sum_{k=1}^{K} m_k(E) \rho^k(x, y) r^k(x, y) \tag{2}$$

where k is the number of tissue types in the object and $r^k(x,y)=1$ if $(x,y) \in$ tissue k and $r^k(x,y)=0$ otherwise.

For the classical pre-processing approach, the object is assumed to consist of a single tissue type (K=1) and to have energy dependence similar to that of water, i.e., $$\mu(x, y, E) = m_1(E) \rho^1(x, y) \tag{3}$$

$$\approx m_w(E) \rho^{soft}(x, y) \tag{4}$$

where $m_w(E)$ is the mass attenuation coefficient of water and $\rho^{soft}$ is the effective soft tissue density. One can rewrite (1) as follows:

$$E[Y_i] = \int I_i(E) e^{-\int_{L_i} \mu(x,y,E) dt} dE \tag{5}$$

-continued $$= \int_{L_i} I_i(E) e^{-m_w(E) \int_{L_i} \rho^{soft}(x,y)} dE$$

$$= \int_{L_i} I_i(E) e^{-m_w(E) T_i} dE \tag{6}$$

$$= F_i(T_i) \tag{7}$$

where $T_i$ is the line integral of the density along path $L_i$. Each function $F_i(T_i)$ i=1, ..., N is 1-1 and monotone decreasing and hence invertible. The goal of the pre-processing method is to estimate $\{T_i\}_{i=1}^{N}$ and from that reconstruct (using FBP) an estimate $\rho(x,y)$ of the energy-independent density $\rho^{soft}$. In other words, $\rho(x,y)$=FBP $\{\hat{T}_i\}$ where $\hat{T}_i = F_i^{-1}(Y_i)$. This pre-processing approach is inaccurate when bone is present, but is often the first step in a post-processing bone correction algorithm.

Post-processing techniques first pre-process and reconstruct the data for soft tissue correction, as explained above. The resulting effective density image is then segmented into bone and soft tissue. This classification enables one to estimate the contributions of soft tissue and bone to the line integrals. These estimates are used to correct for non-linear effects in the line integrals. The final artifact-free image is produced using FBP and displays density values independent of energy according to the following relationship:

$$\hat{\rho}(x,y) = \hat{\rho}^{soft}(x,y) + \lambda_o \hat{\rho}^{bone}(x,y) \tag{8}$$

where $\lambda_o$ is some constant independent of energy that maintains image contrast.

Although post-processing accomplishes its goal of eliminating energy dependence, it suffers from quantitative inaccuracy. As explainer elsewhere, the parameter $\lambda_o$ is somewhat heuristically estimated. In addition, applying post-processing to 3-D or cone-beam geometries can be computationally expensive. Another beam hardening correction of interest is known. This algorithm is iterative (but not statistical). At each pixel, it assumes that the attenuation coefficient is a linear combination of the known attenuation coefficients of two base materials, and it iteratively determines the volume fractions of the base materials. The algorithm depends on an empirically-determined estimate of effective X-ray spectrum of the scanner. The main limitations of this approach is that the spectrum estimate captures the imaging characteristics for a small FOV only and that prior knowledge of the base materials at each pixel is necessary.

Statistical Reconstruction for CT

Many of the inherent shortcomings of FBP are adequately (and naturally) compensated for by statistical methods.

Statistical methods are a subclass of iterative techniques, although the two terms are often used interchangeably in the literature. The broader class of iterative reconstruction techniques includes non-statistical methods such as the Algebraic Reconstruction Technique (ART) which casts the problem as an algebraic system of equations. Successive substitution methods, such as Joseph and Spital's beam-hardening correction algorithm, are also iterative but not statistical. Hence, statistical methods are iterative, but the opposite is not necessarily true.

Statistical techniques have several attractive features. They account for the statistics of the data in the reconstruction process, and therefore lead to more accurate estimates with lower bias and variance. This is especially important in the low-SNR case, where deterministic methods suffer from severe bias. Moreover, statistical methods can be well suited for arbitrary geometries and situations with truncated data. They easily incorporate the system geometry, detector response, object constraints and any prior knowledge. Their main drawback (when compared to FBP) is their longer computational times.

Statistical reconstruction for monoenergetic CT was shown to outperform FBP in metal artifact reduction, in limited-angle tomography and to have lower bias-noise curves.

All single-scan statistical X-ray reconstruction algorithms assume (either implicitly or explicitly) monoenergetic X-ray beams, and thus do not deal with the issue of beam hardening artifacts. The future potential of statistical methods to correct for beam-hardening was speculated by Lange et al. in 1987, but no methods have been proposed for realizing this potential. One exception is the area of dual-energy CT. Dual-energy systems operate based on the principle that the attenuation coefficient can be expressed as a linear combination of two energy basis functions and are capable of providing density images independent of energy.

For X-ray CT images, with typical sizes of 512×512 pixels or larger, statistical methods require very long computational times. This has hindered their widespread use.

The article of Yan et al. in Jan. 2000 IEEE Trans. Med. Im. uses a polyenergetic source spectrum, but it is not statistical and it does not have any regularization. There is no mathematical evidence that their algorithm will converge.

In general, all previous algorithms for regularized statistical image reconstruction of X-ray CT images from a single X-ray CT scan have been either:

1) based explicitly on a monoenergetic source assumption, or
2) based implicitly on such an assumption in that the polyenergetic spectrum and resulting beam hardening effects were disregarded.

SUMMARY OF THE INVENTION

An object of the present invention is to provide a method for reconstructing a polyenergetic X-ray computed tomography image and an image reconstructor apparatus, both of which utilize a statistical algorithm which explicitly accounts for a polyenergetic source spectrum and resulting beam hardening effects.

Another object of the present invention is to provide a method for reconstructing a polyenergetic X-ray computed tomography image and an image reconstructor apparatus, both of which utilize a statistical algorithm which is portable to different scanner geometries.

In carrying out the above objects and other objects of the present invention, a method for statistically reconstructing a polyenergetic X-ray computed tomography image to obtain a corrected image is provided. The method includes providing a computed tomography initial image produced by a single X-ray CT scan having a polyenergetic source spectrum. The initial image has components of materials which cause beam hardening artifacts. The method also includes separating the initial image into different sections to obtain a segmented image and calculating a series of intermediate corrected images based on the segmented image utilizing a statistical algorithm which accounts for the polyenergetic source spectrum and which converges to obtain a final corrected image which has significantly reduced beam hardening artifacts.

The step of calculating may include the steps of calculating a gradient of a cost function having an argument and utilizing the gradient to minimize the cost function with respect to its argument. The step of calculating the gradient may include the step of back projecting. The cost function preferably has a regularizing penalty term.

The step of calculating the gradient may include the step of calculating thicknesses of the components. The step of calculating thicknesses may include the step of reprojecting the segmented image.

The step of calculating the gradient may include the step of calculating means of data along paths and gradients based on the thicknesses of the components.

The argument may be density of the materials at each image voxel.

The method may further include calibrating the spectrum of the X-ray CT scan.

The method may further include displaying the final corrected image.

The step of calculating the gradient may include the step of utilizing ordered subsets to accelerate convergence of the algorithm.

Further in carrying out the above objects and other objects of the present invention, an image reconstructor apparatus for statistically reconstructing a polyenergetic X-ray computed tomography image to obtain a corrected image is provided. The apparatus includes means for providing a computed tomography initial image produced by a single X-ray CT scan having a polyenergetic source spectrum wherein the initial image has components of materials which cause beam hardening artifacts. The apparatus further includes means for separating the initial image into different sections to obtain a segmented image and means for calculating a series of intermediate corrected images based on the segmented image utilizing a statistical algorithm which accounts for the polyenergetic source spectrum and which converges to obtain a final corrected image which has significantly reduced beam hardening artifacts.

The means for calculating may include means for calculating a gradient of a cost function having an argument and means for utilizing the gradient to minimize the cost function with respect to its argument. The cost function preferably has a regularizing penalty term.

The means for calculating the gradient may include means for back projecting.

The means for calculating the gradient may include means for calculating thicknesses of the components.

The means for calculating thicknesses may include means for reprojecting the segmented image.

The means for calculating the gradient may include means for calculating means of data along paths and gradients based on the thicknesses of the components.

The argument may be density of the materials at each image voxel.

The means for calculating the gradient may include means for utilizing ordered subsets to accelerate convergence of the algorithm.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 1 is a schematic view of a basic CT system;

FIGS. 2a–2c are schematic views of various CT geometries wherein FIG. 2a shows a parallel-beam (single ray) arrangement, FIG. 2b shows a fan-beam geometry and FIG. 2c shows a cone-beam arrangement;

BEST MODE FOR CARRYING OUT THE INVENTION

In general, the method and system of the present invention utilize a statistical approach to CT reconstruction and, in particular, iterative algorithms for transmission X-ray CT.

Although the method and system of the invention are described herein for a single-slice fan-beam geometry reconstruction, the method and system may also be used with cone-beam geometries and helical scanning. The method and system may also be used with flat-panel detectors.

Statistical Reconstruction for X-ray CT

The physical and statistical models for the problem of X-ray CT reconstruction is described herein, and an objective function is obtained. Maximizing the objective function by some appropriate iterative algorithm yields the reconstructed image.

Monoenergetic Model and Assumptions

For the purposes of describing the basic principles underlying this invention, for the benefit of skilled practitioners who wish to implement the method, the simplified setting in which the transmission source is monoenergetic is first reviewed. Later the description is generalized to the more realistic polyenergetic case.

The image in object space (attenuation coefficient) is parameterized using square pixels. The goal of the algorithm becomes to estimate the value of the discretized attenuation coefficient at those pixels. Let $\mu=[\mu_1, \ldots, \mu_p]$ be the vector of unknown attenuation coefficients having units of inverse length.

The measurements in a photon-limited counting process are reasonably modeled as independently distributed Poisson random variables. In transmission tomography, the mean number of detected photons is related exponentially to the projections (line integrals) of the attenuation map. The measurements are also contaminated by extra background counts, caused primarily by scatter in X-ray CT. Thus, the following model is assumed for measurements:

$$Y_i \sim \text{Poisson}\{b_i e^{-[A\mu]_i} + r_i\}, i=1, \ldots, N \quad (9)$$

where $b_i = I_i(E_o)$ and N is the number of measurements (or, equivalently, the number of detector bins). The notation $[A\mu]_i = \Sigma_{j=1}^{P} a_{ij} \rho_j$ represents the ith line integral. The N×p matrix $A=\{a_{ij}\}$ is the system matrix which accounts for the system geometry as well as any other significant physical effects such as detector response.

Figure 3:
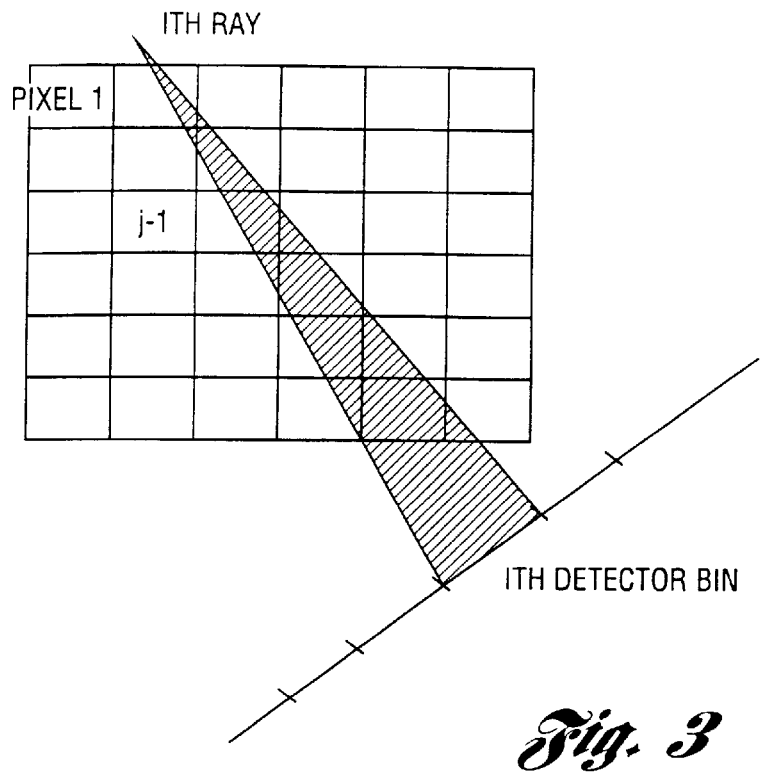
FIG. 3 is a schematic view which illustrates system matrix computation for the fan-beam geometry.

FIG. 3 illustrates one method for computing the elements of A in the fan-beam case. For ray i and pixel j, $a_{ij}$ is the normalized area of overlap between the ray beam and the pixel. The term $r_i$ is the mean number of background events, $b_i$ is the blank scan factor and $Y_i$ represents the photon flux measured by the ith detector. The $Y_i$'s are assumed independent and that $b_i, r_i$ and $\{a_{ij}\}$ are known non-negative constants. $\mu$ is also assumed to be independent of energy.

To find a statistical estimate for the attenuation coefficient vector $\mu$ that is anatomically reasonable, a likelihood-based estimation approach is used. This is a natural choice since the likelihood is based on the statistical properties of the problem. The maximum likelihood (ML) approach also has good theoretical properties. It is asymptotically consistent, unbiased and efficient. The Poisson log likelihood for independent measurements is given by:

$$L(\mu) = \sum_{i=1}^{N} \{Y_i \log(b_i e^{-[A\mu]_i} + r_i) - (b_i e^{-[A\mu]_i} + r_i)\} \quad (10)$$

ignoring constant terms.

Regularization

Without regularization, the Maximum Likelihood (ML) algorithm leads to noisy reconstruction. To reduce noise, it is possible to stop the algorithm when the reconstruction is visually appealing. Another approach is to pre-filter the data or post-filter the reconstruction.

Regularization (penalized-likelihood) approaches for noise reduction have two important advantages. First, the penalty function improves the conditioning of the problem. Second, one can choose penalty functions with certain desirable properties such as edge preservation.

A general form for the regularizing penalty is the following:

$$R(\mu) = \sum_{k=1}^{K} \psi([C\mu]_k) \quad (11)$$

where $\psi$'s are potential functions acting on the soft constraints $C\mu \approx 0$ and K is the number of such constraints. Generally, the potential functions are symmetric, convex, non-negative and differentiable. Non-convex penalties can be useful for preserving edges, but are more difficult to analyze. One can think of the penalty as imposing a degree of smoothness or as a Bayesian prior. Both views are practically equivalent.

Most commonly, penalty function penalize differences in the neighborhood of any particular pixel. They can be expressed as:

$$R(\mu) = \sum_{j=1}^{p} \sum_{k \in N_j} w_{jk} \psi(\mu_j - \mu_k) \quad (12)$$

where the weights $w_{jk}$ are 1 for orthogonal pixels and $$\frac{1}{\sqrt{2}}$$

for diagonal pixels and $N_j$ is the pixel neighborhood.

A common penalty is the quadratic function, $$\psi(x) = \frac{x^2}{2}.$$

This penalty is effective for noise reduction and is analytically simple, but can cause significant blurring, especially at edges. To preserve the edges, one can use a penalty that is less penalizing of large differences. One used herein is the Huber penalty:

$$\psi(x; \delta) = \begin{cases} \frac{x^2}{2}, & x < \delta \\ \delta|x| - \frac{\delta^2}{2}, & x \geq \delta. \end{cases} \quad (13)$$

Figure 4:
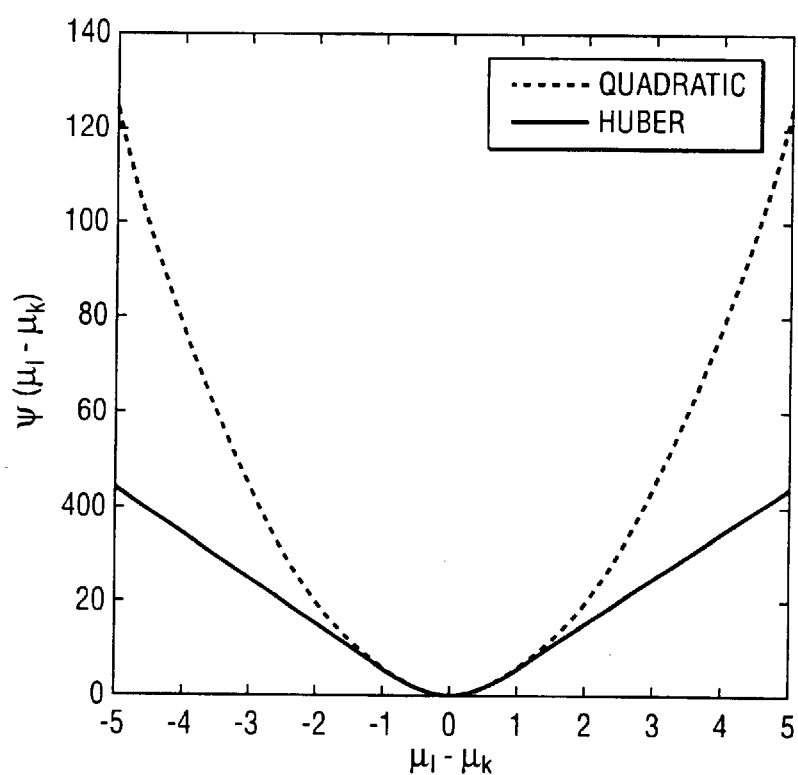
FIG. 4 shows graphs which illustrate convex penalty functions.

A plot of both penalties is shown in FIG. 4.

Combining the ML objective function with a penalty gives a penalized-likelihood (PL) objective function:

$$\Phi(\mu) = L(\mu) - \beta R(\mu). \quad (14)$$

The first term on the right in Equation (14) forces the estimator to match the measured data. The second term imposes some degree of smoothness leading to visually appealing images. The scalar parameter β controls the tradeoff between the two terms (or, alternatively, between resolution and noise).

The goal of the reconstruction technique becomes to maximize (14) subject to certain object constraints such as non-negativity:

$$\hat{\mu} = \underset{\mu \geq 0}{\arg\max} \, \Phi(\mu). \quad (15)$$

Ordered Subsets Transmission Algorithms

The ideal statistical algorithm converges to the solution quickly (in a few iterations) and monotonically. It easily incorporates prior knowledge and constraints, accepts any type of system matrix and is parallelizable. No practical algorithm fits this description, and one settles for some compromise between the conflicting requirements.

Two closely related statistical methods for X-ray CT, namely, the Ordered Subsets Transmission Reconstruction (OSTR) and the Ordered Subsets Penalized Weighted Least Squares (OS-PWLS) algorithms are described herein. OSTR models the sinogram data using Poisson statistics. The randomness in the measurement is a result of the photon emission and detection processes, electronic noise in the current-integrating detectors, as well as background radiation and scatter. Using the Poisson model is important in the low SNR case, since incorrect modeling can lead to reconstruction bias. At high SNR, the noise can be adequately modeled as additive and Gaussian. The additive Gaussian model leads to a least-squares method.

Both methods are based on the optimization transfer principle, which is discussed first. Then, the Poisson transmission model and associated algorithm is developed, including the idea or ordered subsets as a way to accelerate convergence. Although one could develop the least-squares approach from a Gaussian likelihood, it is derived as a quadratic approximation to the Poisson likelihood.

Optimization Transfer Principle

The optimization transfer principle is a very useful and intuitive principle that underlies many iterative methods, including the ones described herein. De Pierro introduced it in the context of inverse problems (emission tomography, to be specific).

Figure 5:
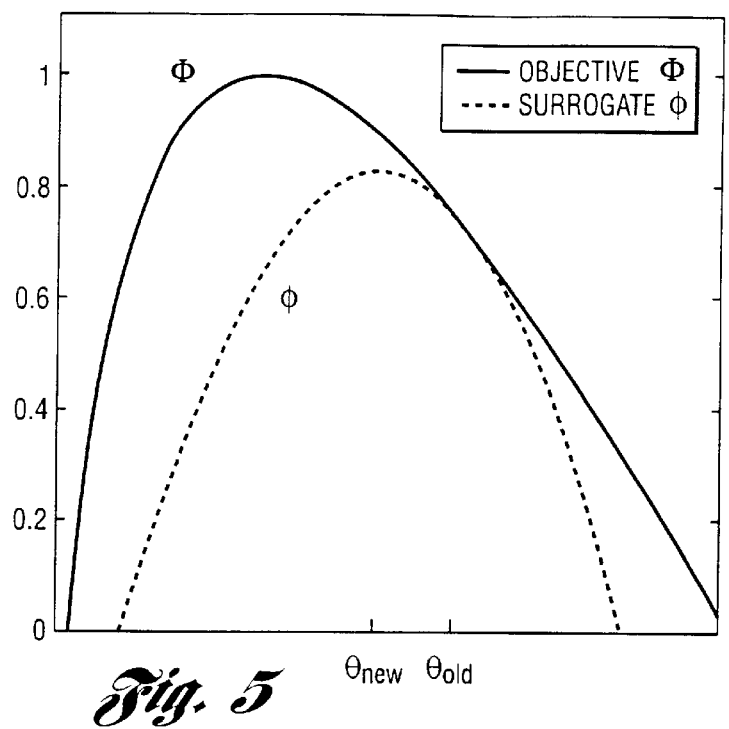
FIG. 5 shows graphs which illustrate the optimization transfer principle.

Often in iterative techniques, the goal is to maximize some objective function $\Phi(\theta)$ with respect to its argument $\theta$. The objective $\Phi(\theta)$ can be difficult to maximize. One resorts to replacing $\Phi$ with a surrogate function $\Phi(\theta;\theta^{(n)})$ that is easier to maximize at each iteration. FIG. 5 illustrates the idea in one-dimension. The full utility of optimization transfer comes into play when the dimension of $\theta$ is large, such as in tomography.

The process is repeated iteratively, using a new surrogate function at each iteration. If the surrogate is chose appropriately, then the maximizer of $\Phi(\theta)$ can be found. Sufficient conditions that ensure that the surrogate leads to a monotonic algorithm are known.

Paraboloidal surrogates are used because they are analytically simple, and can be easily maximized. One can also take advantage of the convexity of these surrogates to parallelize the algorithm.

Separable Paraboloidal Surrogates

Instead of maximizing the log likelihood, one can minimize the negative log likelihood, which is written as:

$$-L(\mu) = \sum_{i=1}^{N} h_i([A\mu]_i) \quad (16)$$

where $h_i(l) = b_i e^{-l} + r_i - Y_i \log(b_i e^{-l} + r_i)$. Direct minimization of (16) leads to noisy estimates, so the likelihood is penalized by adding a roughness penalty. The problem becomes to find an estimate $\hat{\mu}$ such that:

$$\hat{\mu} = \underset{\mu \geq 0}{\arg\min} \, \Phi(\mu) \quad (17)$$

where $$\Phi(\mu) = -L(\mu) + \beta R(\mu). \quad (18)$$

The parameter β controls the tradeoff between the data-fit and penalty terms, and $R(\mu)$ imposes a degree of smoothness on the solution.

When $r_i \neq 0$, the log likelihood is not concave and is difficult to maximize. A monotonic algorithm is possible if the optimization transfer principle is applied with paraboloidal surrogates. Paraboloidal surrogates are used such that the iterates $\mu^n$ monotonically decrease $\Phi$. For that to occur, the surrogate φ must satisfy the following "monotonicity" condition:

$$\Phi(\mu) - \Phi(\mu^n) \leq \phi(\mu^n; \mu^n), \, \forall \mu \geq 0. \quad (19)$$

The following conditions are sufficient to ensure (19):

$$\phi(\mu^n; \mu^n) = \Phi(\mu^n) \tag{20}$$

$$\left.\frac{\partial \phi(\mu; \mu^n)}{\partial \mu_j}\right|_{\mu=\mu^n} = \left.\frac{\partial \phi(\mu)}{\partial \mu_j}\right|_{\mu=\mu^n}, \quad j=1,\ldots,p$$

$$\phi(\mu; \mu^n) \geq \Phi(\mu), \quad \text{for} \quad \mu \geq 0.$$

Attention is restricted to differentiable surrogates. Paraboloidal surrogates are convenient to use because they are easy to minimize. In (16), the likelihood function $h_i(l)$ is replaced with the following quadratic surrogate:

$$q_i(l; l_i^n) \triangleq h_i(l_i^n) + \dot{h}_i(l_i^n)(l - l_i^n) + \frac{1}{2}c_i(l_i^n)(l - l_i^n)^2 \tag{21}$$

where $\dot{h}_i$ is the first derivative of $h_i$. To ensure monotonicity, curvature $c_i$ must be such that the surrogate satisfies the monotonicity conditions (19). Alternatively, to reduce computation, one can pre-compute the $c_i$'s prior to iterating.

Replacing $h_i([A\mu]_i)$ with $q_i([A\mu]_i;[A\mu^n]_i)$ in (16) above will lead to a paraboloidal surrogate for the log likelihood. One can further take advantage of the nature of the surrogate to obtain a separable algorithm, i.e., an algorithm where all pixels are updated simultaneously.

Rewrite the line integral:

$$[A\mu]_i = \sum_{j=1}^p a_{ij}\mu_j = \sum_{j=1}^p \alpha_{ij}\left\{\frac{a_{ij}}{\alpha_{ij}}(\mu_j - \mu_j^n) + [A\mu^n]_i\right\} \tag{22}$$

where $$\sum_{j=1}^p \alpha_{ij} = 1, \quad \forall\ i,\ \alpha_{ij} \geq 0. \tag{23}$$

Using the convexity of $q_i$, and writing $l_i^n = [A\mu^n]_i$, one gets:

$$q_i(([A\mu])_i; l_i^n) \leq \sum_{j=1}^p \alpha_{ij} q_i\left(\frac{a_{ij}}{\alpha_{ij}}(\mu_j - \mu_j^n) + ([A\mu^n])_i; l_i^n\right). \tag{24}$$

The overall separable surrogate for the log likelihood becomes:

$$Q(\mu; \mu^n) = \sum_{i=1}^N \sum_{j=1}^p \alpha_{ij} q_i\left(\frac{a_{ij}}{\alpha_{ij}}(\mu_j - \mu_j^n) + ([A\mu^n])_i; l_i^n\right) \tag{25}$$

$$= \sum_{j=1}^p q_j(\mu_j; \mu^n) \tag{26}$$

where $$q_j(\mu_j; \mu^n) = \sum_{i=1}^N \alpha_{ij} q_i\left(\frac{a_{ij}}{\alpha_{ij}}(\mu_j - \mu_j^n) + ([A\mu^n])_i; l_i^n\right).$$

This formulation decouples the pixels. Each pixel effectively has its own cost function $q_j$. The $q_j$'s can be minimized for all pixels simultaneously, resulting in a parallelizable algorithm.

A similar development can be pursued for the penalty term $R(\mu)$. Taking advantage of the convexity of the potential function yields a separable penalty surrogate $S(\mu;\mu^n)$. One now seeks to minimize the new separable global surrogate:

$$\phi(\mu;\mu^n) \triangleq Q(\mu;\mu^n) + \beta S(\mu;\mu^n). \tag{27}$$

Since the surrogate is a separable paraboloid, it can be easily minimized by zeroing the first derivative. This leads to the following simultaneous update algorithm:

$$\mu_j^{n+1} = \left[\mu_j^n - \frac{\left(\frac{\partial \phi(\mu;\mu^n)}{\partial \mu_j}\right)\Big|_{\mu=\hat{\mu}}}{\left(\frac{\partial^2 \phi(\mu;\mu^n)}{\partial \mu_j^2}\right)\Big|_{\mu=\hat{\mu}}}\right]_+, \quad j=1,\ldots,p \tag{28}$$

where $\hat{\mu}$ is some estimate of $\mu$, usually taken to be the current iterate $\mu^n$. The $[\cdot]_+$ operator enforces the non-negativity constant. From (21) and (25) the first and second derivatives of the surrogate are obtained:

$$\left(\left(\frac{\partial \phi(\mu;\mu^n)}{\partial \mu_j}\right)\Big|_{\mu=\mu^n}\right) = \sum_{i=1}^N a_{ij}\dot{h}_i([A\mu^n]_i; l_i^n) + \beta\left.\frac{\partial S}{\partial \mu_j}\right|_{\mu=\mu^n} \tag{29}$$

$$\left(\left(\frac{\partial^2 \phi(\mu;\mu^n)}{\partial \mu_j^2}\right)\Big|_{\mu=\mu^n}\right) = \sum_{i=1}^N \frac{a_{ij}^2}{\alpha_{ij}}c_i(l_i^n) + \beta\left.\frac{\partial^2 S}{\partial \mu_j^2}\right|_{\mu=\mu^n}. \tag{30}$$

$c_i$ is the surrogate curvature and $\{\alpha_{ij}\}$ satisfies (23). To make the denominator in (28) small (and hence the step size large), one wants $\{\alpha_{ij}\}$ to be large. One also wants $\{\alpha_{ij}\}$ to facilitate convergence, and to be independent of the current iterate so that it can be pre-computed. One convenient choice is:

$$\alpha_{ij} = \frac{a_{ij}}{\sum_{j=1}^p a_{ij}}. \tag{31}$$

It is possible that better choices exist. For the surrogate curvature $c_i$, one can use the optimal one derived in (24). The optimal curvature is iteration dependent. To save computations, one can use the following pre-computed approximation for the curvature:

$$c_i = \ddot{h}_i\left(\log\left[\frac{b_i}{Y_i - r_i}\right]\right). \tag{32}$$

The pre-computed curvature may violate the conditions of monotonicity. It does, however, give an almost-monotonic algorithm, where the surrogate becomes a quadratic approximation of the log likelihood. The pre-computed curvature seems to work well in practice, and the computational savings seem well worth the sacrifice. Major computational savings, however, come from the use of ordered subsets, discussed hereinbelow.

Ordered Subsets

Ordered subsets are useful when an algorithm involves a summation over sinogram indices (i.e., a back projection). The basic idea is to break the set of sinogram angles into subsets, each of which subsamples the sinogram in the angular domain. The back projection process over the complete sinogram is replaced with successive back projections over the subsets of the sinogram. One iteration is complete after going through all of the subsets.

Ordered subsets have been applied to emission tomography with a good degree of success. Improvements in convergence rate by a factor approximately equal to the number of subsets have been reported. Ordered subsets have also been used with transmission data for attenuation map estimation in SPECT. Ordered subsets where applied to the convex algorithm, and an increase in noise level with number of subsets have been reported. Ordered subsets have been used with the transmission EM algorithm and a cone-beam geometry. The OSTR algorithm was originally developed for attenuation correction in PET scans with considerable success.

The choice of ordering the subsets is somewhat arbitrary, but it is preferably to order them "orthogonally." In such an arrangement, the projection corresponding to angles with maximum angular distance from previously chosen angles are used at each step.

The cost of accelerating convergence with ordered subsets is loss of monotonicity. Hence, the term "convergence" is used loosely to mean that one gets visually acceptable reconstruction. Practically speaking, this loss of monotonicity seems to make very little difference for the end result, especially if the algorithm is initialized with a reasonable starting image, such as an FBP reconstruction.

Understanding the convergence properties of ordered subsets can provide insight into additional ways to accelerate convergence that may not be readily apparent.

To summarize, the algorithm thus far flows as follows:

for each iteration n=1, . . . , niter
   for each subset S=1, . . . , M
     compute $h_i([A\hat{\mu}])$
     compute $c_i([A\hat{\mu}])$ (or use pre-computed value)
     $L_j = M\Sigma_{i \in S} a_{ij} h_i$, j=1, . . . , p
     $d_j = M\Sigma_{i \in S} a_{ij} \gamma_i c_i$, j=1, . . . , p $$*\hat{\mu} = \left[\hat{\mu}_j - \frac{\left(L_j + \beta \frac{\partial S}{\partial \mu_j}\Big|\right)_{\mu=\mu_{old}}}{\left(d_j + \beta \frac{\partial^2 S}{\partial \mu_j^2}\Big|\right)_{\mu=\mu_{old}}}\right]_+, \quad j=1, \ldots, p$$

end
end

Scaling the denominator and numerator by the number of subsets ensures that the regularization parameter β remains independent of the number of subsets. This algorithm is known as the Ordered Subsets Transmission Reconstruction (OSTR) algorithm.

OSTR combines the accuracy of statistical reconstruction with the accelerated rate of convergence that one gets from ordered subsets. The separability of the surrogates makes the algorithm easily parallelizable. The algorithm also naturally enforces the non-negativity constraint. The monotonicity property has been satisfied, but that seems to hardly make a difference in practice if a reasonable starting image is used.

Penalized Weighted Least Squares with Ordered Subsets

Figure 6:
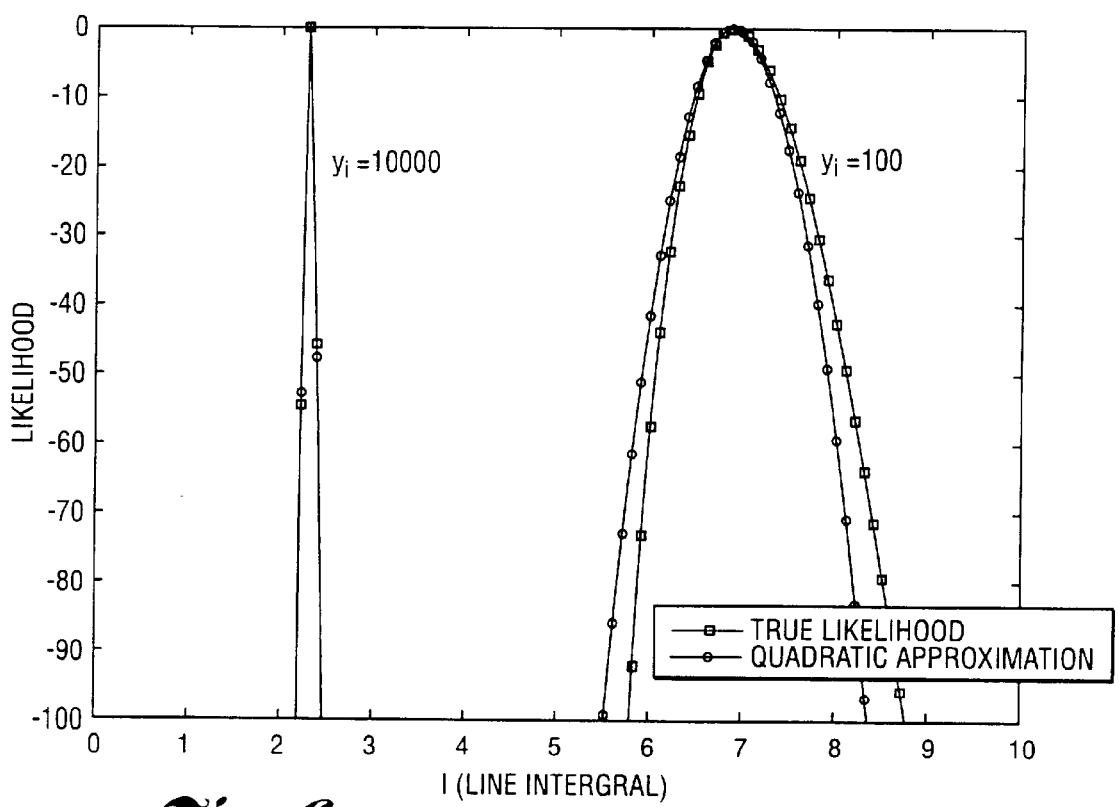
FIG. 6 shows graphs which are quadratic approximations to the Poisson log likelihood.
Figure 7:
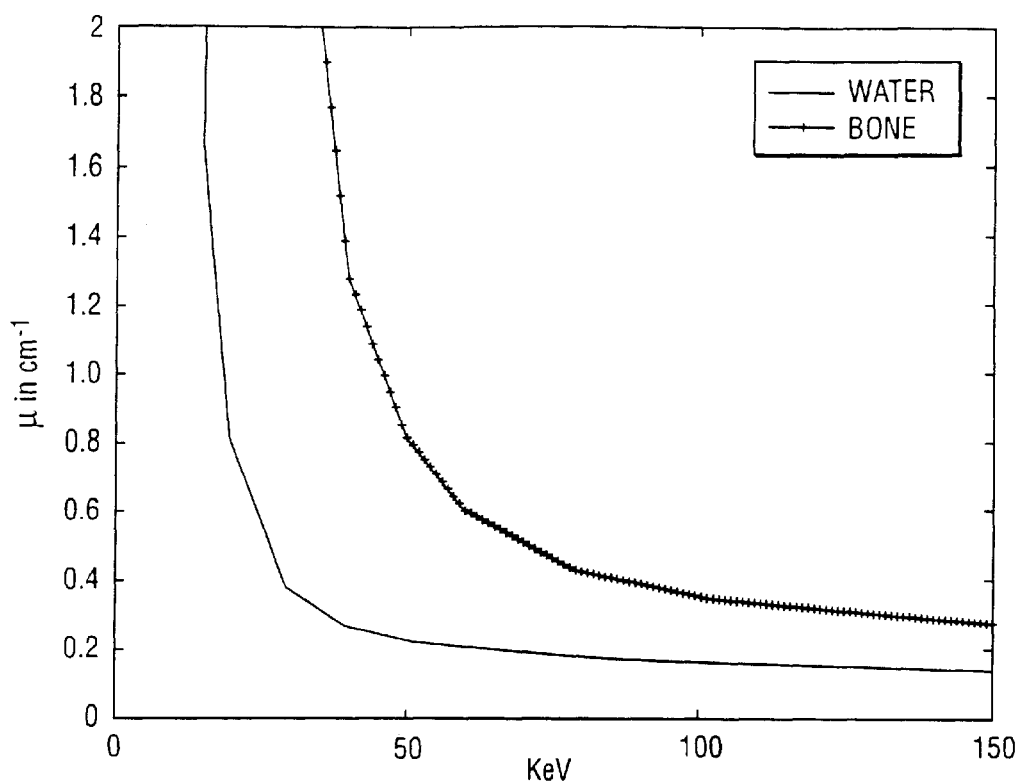
FIG. 7 shows graphs which illustrate attenuation coefficient energy dependence.
Figure 8:
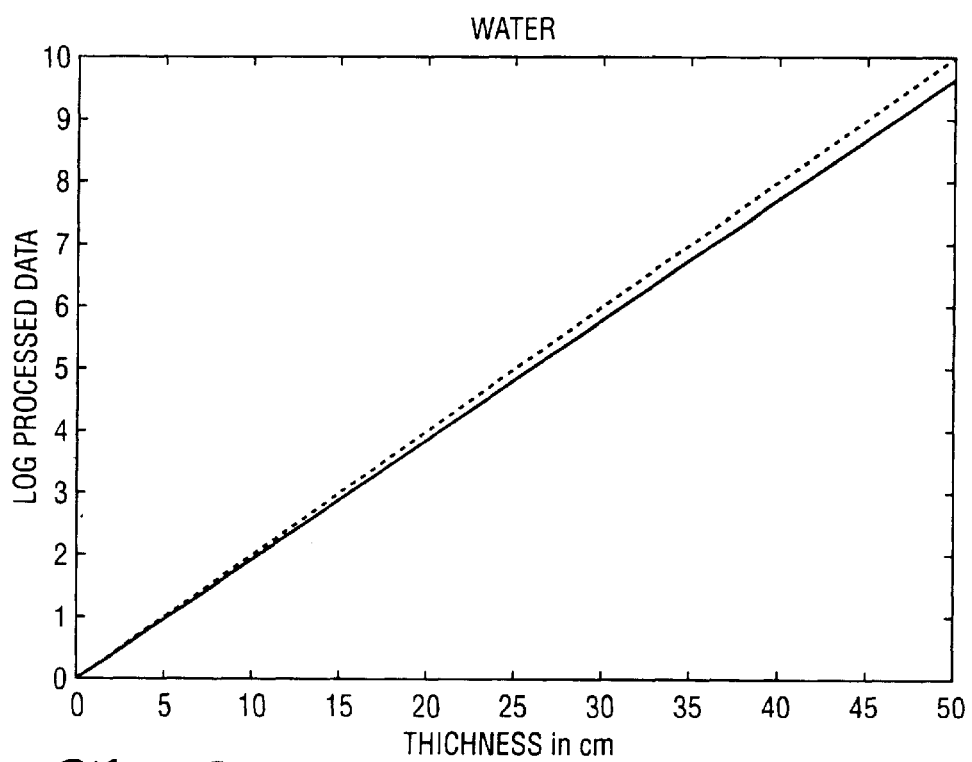
FIG. 8 shows graphs which illustrate beam hardening induced deviation of line integral from linearity in water.
Figure 9:
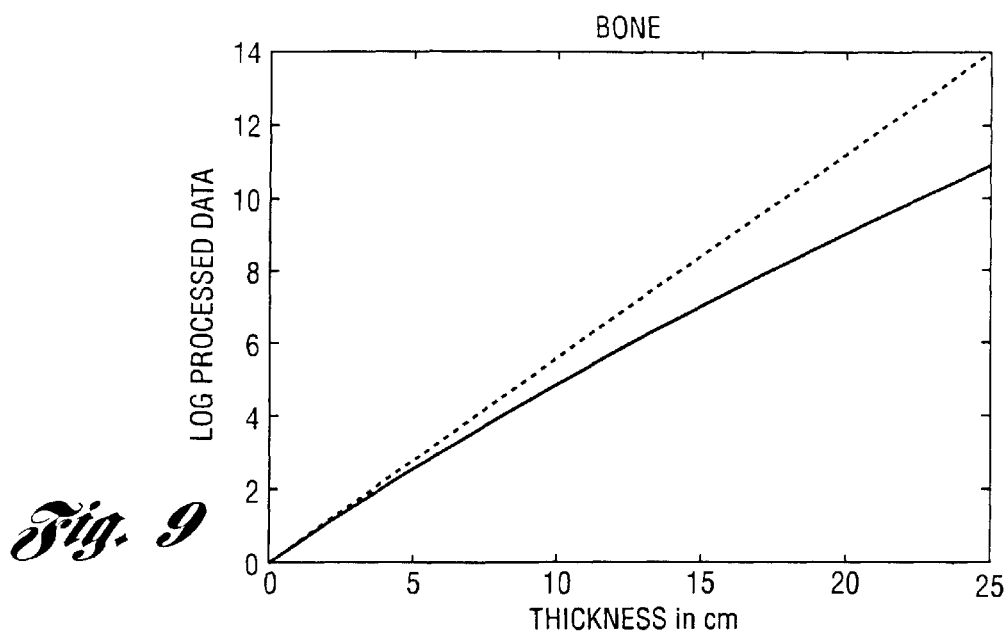
FIG. 9 shows graphs which illustrate beam hardening induced deviation of line integral from linearity in bone.

OSTR uses Poisson statistics to model the detection process. For high SNR scans, the Gaussian model is a reasonable approximation to the Poisson distribution. The Gaussian model leads to a simpler quadratic objection function and weighted-least-squares minimization. With high counts, PWLS leads to negligible bias and the simpler objective function reduces computation time. FIG. 6 illustrates how the quadratic approximation to the likelihood improves with count number.

The algorithm is reformulated by deriving a quadratic approximation to the Poisson likelihood, which leads to a simpler objective function. The regularization term and the use of ordered subsets are retained. This variation of the method of the invention is called Ordered Subset Penalized Weight Least Squares (OS-PWLS).

For convenience, the negative log likelihood for transmission data is rewritten:

$$-L(\mu) = \sum_{i=1}^{N} h_i([A\mu]_i) \tag{33}$$

$$= \sum_{i=1}^{N} \{-Y_i \log(b_i e^{-[A\mu]_i} + r_i) + b_i e^{-[A\mu]_i} + r_i)\}. \tag{34}$$

Taylor's expansion is applied to $h_i(l_i)$ around some value $\hat{l}_i$ and first and second order terms only are retained.

$$h_i(l_i) \approx h_i(\hat{l}_i) + \dot{h}_i(\hat{l}_i)(l_i - \hat{l}_i) + \frac{\ddot{h}_i(\hat{l}_i)}{2}(l_i - \hat{l}_i)^2 \tag{35}$$

where $\dot{h}_i$ and $\ddot{h}_i$ are the first and second derivatives of $h_i$. Assuming $Y_i > r_i$, one can estimate the line integral with:

$$\hat{l}_i = \log\left(\frac{b_i}{Y_i - r_i}\right). \tag{36}$$

Substituting this estimate in (35) gives the following approximation for $h_i$:

$$h_i(l_i) \approx (Y_i - Y_i \log Y_i) + \frac{w_i}{2}(l_i - \hat{l}_i)^2. \tag{37}$$

The first term in (37) is independent of $l_i$ and can be dropped. The weight is $$w_i = \frac{(Y_i - r_i)^2}{Y_i}.$$

The new objective function is:

$$\Phi_q(\mu) = \sum_{i=1}^{N} \frac{w_i}{2} ([A\mu]_i - \hat{l}_i)^2 + \beta R(\mu). \tag{38}$$

The subscript $q$ indicates that this objective function is based on a quadratic approximation to the log likelihood. Subsequently, the subscript is dropped. The penalty term is also added. Minimizing this objective function over $\mu \geq 0$ will lead to an estimator with negligible bias, since the number of counts is large.

A separable surrogate for the objective function is almost immediately available. The terms inside the objective function summation are all convex. This convexity "trick" is explored yet one more time. Along the lines of (24) and (25), the surrogate for the PWLS objective function is:

$$Q_q(\mu; \mu^n) = \sum_{i=1}^{N}\sum_{j=1}^{P} a_{ij} \frac{w_i}{2}\left(\frac{a_{ij}}{\alpha_{ij}}(\mu_j - \mu_j^n) + ([A\mu^n])_i - \hat{l}_i\right)^2 \quad (39)$$

$$= \sum_{j=1}^{p} q_{j,q}(\mu_j; \mu_j^n). \quad (40)$$

The subscript $_q$ again emphasizes that this surrogate resulted from the quadratic approximation to the likelihood. It is dropped to simplify notation. A surrogate for the penalty function can be derived in a similar manner and added to (40).

To use the iterative update (28) to minimize the surrogate, its first and second derivatives are computed, and the computational savings of the PWLS algorithm is demonstrated.

$$\left.\frac{\partial Q(\mu; \mu^n)}{\partial \mu_j}\right|_{\mu=\mu^n} = \sum_{i=1}^{N} a_{ij} w_i ([A\mu^n]_i - \hat{l}_i) \quad (41)$$

$$\left.\frac{\partial^2 Q(\mu; \mu^n)}{\partial \mu_j^2}\right|_{\mu=\mu^n} = \sum_{i=1}^{N} \frac{a_{ij}^2 w_i}{\alpha_{ij}}. \quad (42)$$

Unlike $\dot{h}_i$ term in (29), the numerator (first derivative) in (41) involves no exponential terms and the denominator (second derivative) in (42) can be pre-computed and stored. The sum over sinogram indices can also be broken into sums over ordered subsets, further accelerating the algorithm.

The iterative update is rewritten with the changes resulting from OS-PWLS:

$$\hat{\mu}_j = \left[\hat{\mu}_j - \frac{M\sum_i a_{ij} w_i ([A\hat{\mu}]_i - \hat{l}_i) + \beta \left.\frac{\partial S}{\partial \mu_j}\right|_{\mu=\mu_{old}}}{M\sum_i \frac{a_{ij}^2 w_i}{\alpha_{ij}} + \beta \left.\frac{\partial^2 S}{\partial \mu_j^2}\right|_{\mu=\mu_{old}}}\right]_+ . \quad (43)$$

Both OSTR and OS-PWLS have been described above for the monoenergetic case. The more realistic case of multi-energetic X-ray beam is described hereinbelow and a correction scheme is incorporated into OS-PWLS for the artifacts caused by the broad beam spectrum.

Statistical Reconstruction for Polyenergetic X-ray CT

One of the strengths of statistical methods is their applicability to different system and physical models. The CT transmission model is generalized hereinbelow to account for the broad spectrum of the beam. From the model, a cost function is derived and an iterative algorithm is developed for finding the minimizer of the cost function.

Polyenergetic Statistical Model for CT

A model for X-ray CT is described now that incorporates the energy dependence of the attenuation coefficient. A prior art algorithm could be applied to an image reconstructed with OS-PWLS. Instead, beam hardening correction is developed as an integral element of the statistical algorithm. The object is assumed to be comprised of K non-overlapping tissue types (this assumption may be generalized to allow for mixtures of tissues). For example, when K=2, one can use soft tissue and bone tissue classes, and when K=3, one can use soft tissue, bone, and a contrast agent, such as iodine. An iterative algorithm that generalizes OS-PWLS naturally emerges from the model.

Assume that the K tissue classes are determined by pre-processing the data with soft tissue correction and then segmenting an initial reconstructed image. The object model of (2) is restricted to two spatial dimensions:

$$\mu(x, y, E) = \sum_{k=1}^{K} m_k(E) \rho^k(x, y) r^k(x, y). \quad (44)$$

The system matrix is denoted with $A=\{a_{ij}\}$ and the following definitions are made:

$$R_k \triangleq \{\text{set of pixels classified as tissue type } k\}, \quad (45)$$

$$r^k = [r_1^k, \ldots, r_p^k] \quad \text{where} \quad \begin{cases} r_j^k = 1, & j \in R_k \\ r_j^k = 0, & \text{otherwise,} \end{cases} \quad (46)$$

$$s_i^k(\rho) \triangleq \int_{L_i} \rho^k(x, y) r^k(x, y) dl, \quad (47)$$

The mass attenuation coefficients $\{m_k(E)\}_{k=1}^{K}$ of each of the K tissue types are assumed to be known. Discretization aside, from (1) the mean of the measured data along path $L_i$ is:

$$E[Y_i] = \int I_i(E) e^{-\sum_{k=1}^{K} m_k(E) \int_{L_i} \rho^k(x,y) dl} dE \quad (49)$$

$$= \int I_i(E) e^{-\sum_{k=1}^{K} m_k(E) s_i^k(\rho)} dE$$

$$= \int I_i(E) e^{-\underline{m}'(E) \underline{v}_i(\rho)} dE$$

$$\triangleq \overline{Y}_i(\underline{v}_i(\rho))$$

where $\underline{m}(E)=[m_1(E), \ldots, m_K(E)]$ and the $\Delta$ stands for vector transpose. The measurements are expressed as a function of the column vector quantity $\underline{v}_i$ which has its elements the line integrals of the K different tissue densities. From knowledge of the X-ray spectrum, the values of $\overline{Y}_i(\underline{v}_i)$ and its gradient $\nabla \overline{Y}_i(\underline{v}_i)$ are tabulated. In the discrete domain, $$s_i^k(\rho) = \sum_{j=1}^{p} a_{ij} r_j^k \rho_j. \quad (50)$$

The goal of the algorithm is to estimate the density coefficient vector $\rho=[\rho_1, \ldots, \rho_p]$. Rather than estimating K vector quantities of length $\rho$, each representing the density of one kind of tissue, the non-overlapping assumption of the tissue types enables one to keep the number of unknowns equal to p, as is the case in the monoenergetic model. This is possible when prior segmentation of the object is available. This can be obtained from a good FBP image, for example.

Polyenergetic Model Cost Function

The Poisson log likelihood is set up in terms of the density $\rho$ and the vector $\underline{v}_i$. To get a quadratic cost function, one follows a similar procedure to that described hereinabove, using the second-order Taylor's expansion.

The function $\overline{Y}_i$ represents the expected value of the measurement $Y_i$ at the ith detector. Using $\overline{Y}_i$ in (10) gives the following negative log likelihood:

$$-L(\rho) = \sum_{i=1}^{N} h_i(\underline{v}_i(\rho)) \quad (51)$$

$$h_i(\underline{v}_i(\rho)) \triangleq -Y_i \log[\overline{Y}_i(\underline{v}_i(\rho)) + r_i] + (\overline{Y}_i(\underline{v}_i(\rho)) + r_i) \quad (52)$$

The problem now is to find an estimate $\hat{\rho}$ such that:

$$\hat{\rho} = \operatorname*{argmin}_{\rho \geq 0} \Phi(\rho) \quad (53)$$

where $$\Phi(\rho) = -L(\rho) + \beta R(\rho). \quad (54)$$

The regularization term can be treated exactly as before or it can be modified to avoid smoothing between different tissue types. For now, one focuses on the likelihood term and set the background term $r_i=0$.

Suppose one can determine some initial estimate of $\underline{v}_i(\rho)$, denoted $\underline{\hat{v}}_i = (\hat{s}_i^1, \ldots, \hat{s}_i^K)$. One expands $h_i(\underline{v}_i(\rho))$ in a second-order Taylor series around $\underline{\hat{v}}_i$:

$$h_i(\underline{v}) \approx h_i(\underline{\hat{v}}_i) + \nabla h_i(\underline{\hat{v}}_i)(\underline{v} - \underline{\hat{v}}_i) + \frac{1}{2}(\underline{v} - \underline{\hat{v}}_i)' \nabla^2 h_i(\underline{\hat{v}}_i)(\underline{v} - \underline{\hat{v}}_i). \quad (55)$$

Taking the first and second derivatives of $h_i(\underline{v}) = -Y_i \log \overline{Y}_i(\underline{v}) + \overline{Y}_i(\underline{v})$, one gets the following for the first and second order terms of the Taylor expansion:

$$\nabla h_i(\underline{v}) = \left(1 - \frac{Y_i}{\overline{Y}_i(\underline{v})}\right) \nabla \overline{Y}_i(\underline{v}) \quad (56)$$

$$\nabla^2 h_i(\underline{v}) = \left(1 - \frac{Y_i}{\overline{Y}_i(\underline{v})}\right) \nabla^2 \overline{Y}_i(\underline{v}) + \frac{Y_i}{\overline{Y}_i^2(\underline{v})} \nabla' \overline{Y}_i(\underline{v}) \nabla \overline{Y}_i(\underline{v}). \quad (57)$$

The gradient $\nabla h_i$ is a row vector and the Laplacian operator $\nabla^2$ gives a K×K matrix of partial derivatives.

To simplify the algorithm and maintain the desirable property of separability, $Y_i$ is assumed to be close enough to $\overline{Y}_i(\underline{\hat{v}}_i)$ for one to drop the first term on the right of (57). This also ensures that the resulting Hessian approximation is non-negative definite.

In the Taylor expansion (55), the first term is constant and does not affect minimnization, so it is dropped. The following is a quadratic approximation to the negative log likelihood:

$$-L(\rho) \approx \Phi_q(\rho) \triangleq \sum_{i=1}^{N} \nabla h_i(\underline{\hat{v}}_i)(\underline{v}_i(\rho) - \underline{\hat{v}}_i) + \quad (58)$$

$$\frac{1}{2Y_i}(\underline{v}_i(\rho) - \underline{\hat{v}}_i)' \nabla' \overline{Y}_i(\underline{\hat{v}}_i) \nabla \overline{Y}_i(\underline{\hat{v}}_i)(\underline{v}_i(\rho) - \underline{\hat{v}}_i)$$

$$= \sum_{i=1}^{N} \nabla h_i(\underline{\hat{v}}_i)(\underline{v}_i(\rho) - \underline{\hat{v}}_i) + \frac{1}{2Y_i}(\nabla \overline{Y}_i(\underline{\hat{v}}_i)(\underline{v}_i(\rho) - \underline{\hat{v}}_i))^2. \quad (59)$$

Substituting (50) into (59) and expanding the vector inner product yields:

$$\Phi_q(\rho) = \quad (60)$$
$$\sum_{i=1}^{N} \left\{ \sum_{k=1}^{K} \frac{\partial h_i}{\partial s_i^k}(\underline{\hat{v}}_i)(s_i^k(\rho) - \hat{s}_i^k) + \frac{1}{2Y_i}\left[\sum_{k=1}^{K} \frac{\partial \overline{Y}_i}{\partial s_i^k}(\underline{\hat{v}}_i)(s_i^k(\rho) - \hat{s}_i^k)\right]^2 \right\}$$

$$= \sum_{i=1}^{N} \left\{ \sum_{k=1}^{K} \nabla_k h_i(\underline{\hat{v}}_i)(s_i^k(\rho) - \hat{s}_i^k) + \frac{1}{2Y_i}\left[\sum_{k=1}^{K} \nabla_k \overline{Y}_i(\underline{\hat{v}}_i)(s_i^k(\rho) - \hat{s}_i^k)\right]^2 \right\}, \quad (61)$$

where $\nabla k$ denotes the kth element of the gradient vector. To simplify the above equation, the following definitions are made:

$$Z_i \triangleq \sum_{k=1}^{K} \nabla_k \overline{Y}_i(\underline{\hat{v}}_i) \hat{s}_i^k = \nabla \overline{Y}_i(\underline{\hat{v}}_i) \underline{\hat{v}}_i,$$

$$b_{ij} \triangleq \sum_{k=1}^{K} \nabla_k \overline{Y}_i(\underline{\hat{v}}_i) a_{ij} r_j^k,$$

$$B \triangleq \sum_{k=1}^{K} D(\nabla_k \overline{Y}_i(\underline{\hat{v}}_i)) A D(\underline{r}^k).$$

$A = \{a_{ij}\}$ is the geometrical system matrix. The matrix $B = \{b_{ij}\}$ is a weighted system matrix, with the weights expressed as the non-zero elements of a diagonal matrix $D(\cdot)$, to the left of A. The term $Z_i$ combines constants independent of $\rho$. With the above definitions, expressing the line integrals explicitly in terms of the image pixels yields the following form of the cost function:

$$\Phi_q(\rho) = \sum_{i=1}^{N} \left\{ \sum_{k=1}^{K} \nabla_k h_i(\underline{\hat{v}}_i) \left( \sum_{j=1}^{P} a_{ij} r_j^k (\rho_j - \hat{\rho}_j) \right) + \frac{1}{2Y_i}\left( \sum_{j=1}^{P} b_{ij} \rho_j - Z_i \right)^2 \right\} + \beta R(\rho). \quad (62)$$

This cost function is convex, so a separable surrogate and an iterative update are easily derived as described above. The results of the algorithm derivation are described below.

The separable paraboloidal surrogate for $\Phi_q(\rho)$ is given by:

$$Q(\rho; \rho^n) = \sum_{j=1}^{P} \sum_{i=1}^{N} \sum_{k=1}^{K} \nabla_k h_i(\underline{\hat{v}}_i) a_{ij} r_j^k \rho_j - \quad (63)$$

$$\sum_{i=1}^{N} \sum_{k=1}^{K} \nabla_k h_i(\underline{\hat{v}}_i) a_{ij} r_j^k \hat{\rho}_j +$$

$$\sum_{j=1}^{P} \sum_{i=1}^{N} \frac{1}{2Y_i} \alpha_{ij} \left( \frac{b_{ij}}{\alpha_{ij}}(\rho_j - \rho_j^n) + [B\rho^n]_i - Z_i \right)^2 +$$

$$\beta S(\rho; \rho^n)$$

where $$\alpha_{ij} \triangleq \frac{b_{ij}}{\sum_{j=1}^{P} b_{ij}}.$$

Setting the point of linearization of the Taylor series at $\rho^n$, and evaluating the first and second derivative of Q at the same point gives:

$$\left.\frac{\partial Q(\rho;\rho^n)}{\partial \rho_j}\right|_{\rho=\rho^n} = \sum_{i=1}^{N}\sum_{k=1}^{K} a_{ij} r_j^k \nabla_k h_i(\hat{v}_i) + \beta \left.\frac{\partial S}{\partial \mu_j}\right|_{\rho=\rho^n} \quad (64)$$

$$\left.\frac{\partial^2 Q(\rho;\rho^n)}{\partial \rho_j^2}\right|_{\rho=\rho^n} = \sum_{i=1}^{N} \frac{1}{\bar{Y}_i}\frac{b_{ij}^2}{\alpha_{ij}} + \beta \left.\frac{\partial^2 S}{\partial \mu_j^2}\right|_{\rho=\rho^n} . \quad (65)$$

The overall algorithm is:
initialize with $\hat{\rho}$.
   for each iteration n=1, . . . , niter
   for each subset S=1, . . . , M compute $\hat{s}_i^k = \sum_{j=1}^{p} a_{ij} r_j^k \hat{\rho}_j$ for $k = 1, \ldots, K$, $\hat{v}_i = [\hat{s}_i^1, \ldots, \hat{s}_i^K]$ compute $\bar{Y}_i(\hat{v}_i)$, its gradient vector $\nabla \bar{Y}_i(\hat{v}_i)$ and $h_i(\hat{v}_i)$ compute $b_{ij} \sum_{k=1}^{K} \nabla_k \bar{Y}_i(\hat{v}_i) a_{ij} r_j^k$ compute $d_j = \sum_{i \in S} \frac{1}{\bar{Y}_i}\frac{b_{ij}^2}{\alpha_{ij}}$ compute $\hat{N}_j = \sum_{i \in S}\sum_{k=1}^{K} a_{ij} r_j^k \nabla_k h_i(\hat{v}_i)$ compute $$\hat{\rho}_j = \left[\hat{\rho}_j - \frac{M\hat{N}_j + \beta \left.\frac{\partial S}{\partial \rho_j}\right|_{\rho=\hat{\rho}}}{M d_j + \beta \left.\frac{\partial^2 S}{\partial \rho_j^2}\right|_{\rho=\hat{\rho}}}\right]_+ \quad j = 1, \ldots, p \quad (66)$$

-end end

This algorithm globally converges to the minimizer of the cost function $\Phi_q(\rho)$ when one subset is used, provided the penalty is chosen so that $\Phi_q$ is strictly convex. When two or more subsets are used, it is expected to be monotone in the initial iterations.

Figure 10:
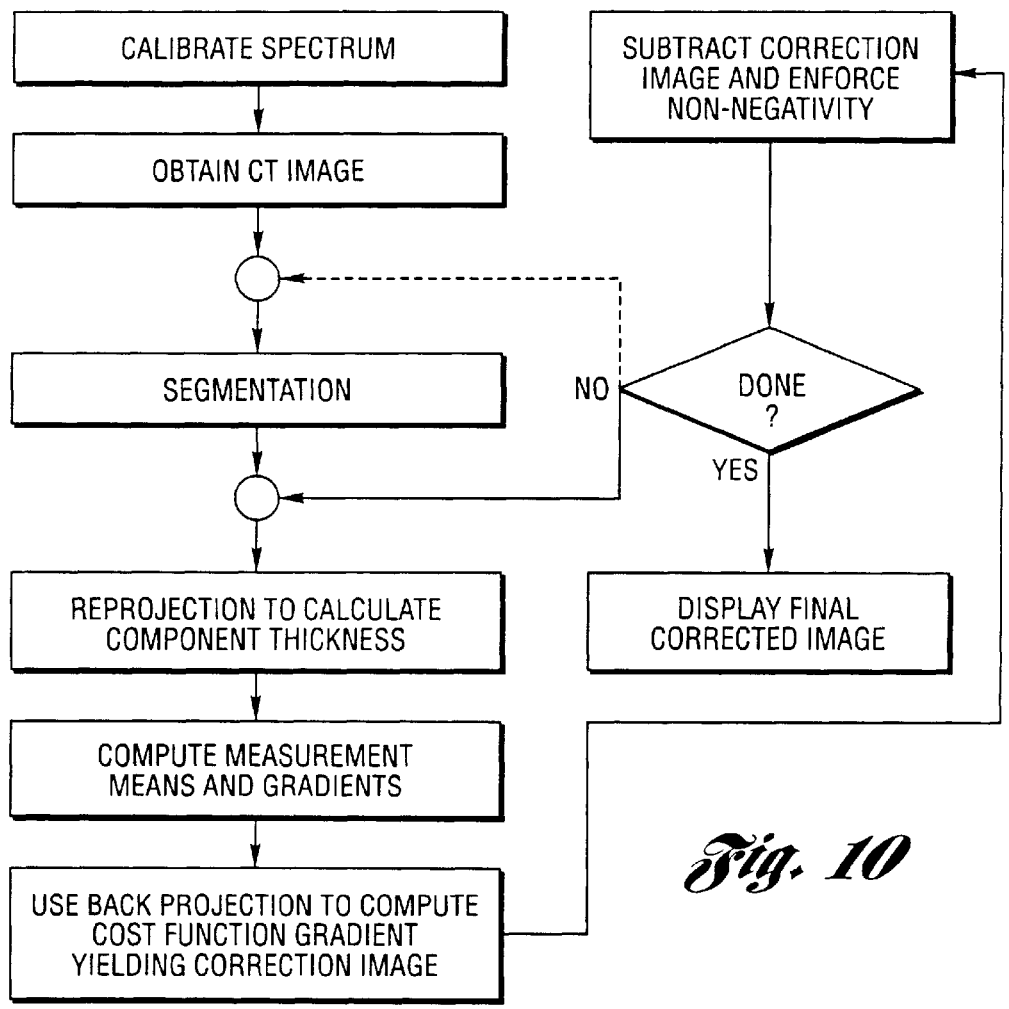
FIG. 10 is a block diagram flow chart of the method of the present invention.

Referring now to FIG. 10, there is illustrated in block diagram flow chart form, the method of the present invention.

Initially, the spectrum of the incident X-ray beam is calibrated.

Then, the initial CT image is obtained.

Segmentation of the CT image is then performed.

Reprojection of the segmented image to calculate each component thickness is performed.

Then, measurement means and gradients are calculated as described above.

Then, a cost function gradient is computed using back projection to yield the correction image as also described above.

The correction image is then subtracted and non-negativity is enforced.

The number of iterations is checked against a predetermined number or other criteria and if the iterative part of the method is complete, then the final corrected image is displayed. If not done, the iterative part of the method is re-entered at the reprojection step. At least some of the results obtained after subtraction may be used in the segmentation step as described herein as indicated by the dashed line from the "DONE" block.

Realistically, many pixels are not comprised of one tissue only, but can be a mixture of several substances. This fact and the errors it causes in CT reconstruction, known as the partial volume effect, must be addressed for more accurate CT images. The method and apparatus described above are generalizable to the case of voxel mixtures by using fractional values in equation (46). It is possible to use histogram information to determine the value of the attenuation coefficient as a probabilistically weighted sum of several tissue types. Combining multi-energy measurements with tissue characteristics may also lead to more accurate "mixel models", where a pixel contains a tissue mixture.

Algorithm

So far, beam hardening correction in the method of the invention depends on the availability of accurate classification of the different substances in the object. In simulated phantom studies, the bone/tissue distribution was known exactly. In a more realistic setting, such a classification would be available from segmenting an initial image reconstructed with FBP. Using this segmentation map for all iterations may adversely affect the accuracy of the reconstruction.

One promising alternative approach is to use joint likelihoods and penalties to estimate both pixel density values and tissue classes. In such an approach, the tissue classes are treated as random variables with a Markov random field model and are estimated jointly with the attenuation map. The joint likelihood will be a function of both the pixel density value and the pixel class. The joint penalties involve two parameters that balance the tradeoff between data fit and smoothness. In addition, joint penalties must account for the fact that pixels tend to have similar attenuation map values if the underlying tissue classes are the same, and vice versa. Such penalties would encourage smoothness in the same region but allow discontinuities between regions of different tissues.

Computation Time

The long computation times of statistical methods hinder their use in clinical X-ray CT applications. Significant acceleration by using ordered subsets have been demonstrated.

From the algorithm design perspective, minor modifications may be made to accelerate convergence. Another possibility is to use a hybrid class of methods, which combines the faster early convergence rate of gradient methods with the faster ultimate linear convergence rate of steepest descent.

The most computationally expensive components of the iterative algorithm are back projection and forward projection, and there are algorithms that claim to perform these operations very quickly. It is possible that customized hardware may be used to perform the projections. Some recent work showed that readily available 2-D texture mapping hardware speeds up the Simultaneous Algebraic Reconstruction Technique (SART) to almost real-time realizations. SART involves forward and back projections much like OS-PWLS does.

Computation time may be reduced by using Fourier domain methods, where the 2-D Fourier transform of the image is assembled from its projections. The practicality of this approach depends on the availability of fast gridding methods in the Fourier domain.

Scatter

Scatter is a major problem in cone-beam CT, where it can range from 40% up to 200% of the unscattered data. Collimation reduces scatter, but collimating flat-panel detectors is challenging. Among several factors that affect the performance of a cone-beam, flat-panel detector computed tomography system, scatter was shown to degrade the detector quantum efficiency (DQE) and to influence the optimal magnification factor. Larger air gaps were needed to cope with high scatter, especially if imaging a large FOV.

There are generally two approaches to dealing with the problem of scatter. Scatter can either be physically removed (or reduced) before detection or can be numerically estimated and its effect compensated for. Ways to physically remove scatter include air gaps and grids, but are not very practical once flat-panel detectors are used, due to the small size of detector pixels.

There are several approaches to numerically estimate scatter. For example, idle detectors (those outside FOV) can be used to provide a scatter estimate. Such measurements can be combined with analytic models for scatter that depend, among other factors, on the energy of the radiation used, the volume of scattering material and system geometry.

There have also been encouraging attempts at incorporating scatter estimation/correction into statistical reconstruction. For instance, ordered subsets EM methods with scatter correction gave superior results to FBP with scatter correction in emission CT. In another work, the maximum likelihood EM algorithm successfully improved contrast and SNR of digital radiology images by incorporating a convolution-based scatter estimate. This is particularly relevant since cone-beam transmission CT with flat-panel detectors is in many ways similar to digital radiography. It is, in essence, a rotating digital radiography system.

A scatter estimate may be incorporated in the model of the CT problem as well as in the reconstruction algorithm using the ri terms above. One approach to scatter estimation and correction is a numerical one, i.e., ways to physically eliminate scatter will not be considered. This makes the approach portable to different systems, and less costly.

System Design

The statistical measurement model has the potential to be extended to take into account the time dimension when imaging the heart, and thus free the designer from synchronization constraints. Moreover, statistical reconstruction eliminates the need for rebinning and interpolation. This may lead to higher helical scanning pitch and cardiac imaging with good temporal and axial resolutions.

Conclusion

In conclusion, a framework has been described above for using statistical methods to reconstruct X-ray CT images from polyenergetic sources.

While the best mode for carrying out the invention has been described in detail, those familiar with the art to which this invention relates will recognize various alternative designs and embodiments for practicing the invention as defined by the following claims.

What is claimed is:

1. A method for statistically reconstructing a polyenergetic X-ray computed tomography image to obtain a corrected image, the method comprising:

providing a computed tomography initial image produced by a single X-ray CT scan having a polyenergetic source spectrum wherein the initial image has components of materials which cause beam hardening artifacts;

separating the initial image into different sections to obtain a segmented image; and calculating a series of intermediate corrected images based on the segmented image utilizing a statistical algorithm which accounts for the polyenergetic source spectrum and which converges to obtain a final corrected image which has significantly reduced beam hardening artifacts.

2. The method as claimed in claim 1 wherein the step of calculating includes the steps of calculating a gradient of a cost function having an argument and utilizing the gradient to minimize the cost function with respect to its argument.

3. The method as claimed in claim 2 wherein the step of calculating the gradient includes the step of back projecting.

4. The method as claimed in claim 2 wherein the step of calculating the gradient includes the step of calculating thicknesses of the components.

5. The method as claimed in claim 4 wherein the step of calculating thicknesses includes the step of reprojecting the segmented image.

6. The method as claimed in claim 4 wherein the step of calculating the gradient includes the step of calculating means of data along paths and gradients based on the thicknesses of the components.

7. The method as claimed in claim 2 wherein the argument is density of the materials at each image voxel.

8. The method as claimed in claim 1 further comprising calibrating the spectrum of the X-ray CT scan.

9. The method as claimed in claim 1 further comprising displaying the final corrected image.

10. The method as claimed in claim 2 wherein the step of calculating the gradient includes the step of utilizing ordered subsets to accelerate convergence of the algorithm.

11. The method as claimed in claim 2 wherein the cost function has a regularizing penalty term.

12. An image reconstructor apparatus for statistically reconstructing a polyenergetic X-ray computed tomography image to obtain a corrected image, the apparatus comprising:

means for providing a computed tomography initial image produced by a single X-ray CT scan having a polyenergetic source spectrum wherein the initial image has components of materials which cause beam hardening artifacts;

means for separating the initial image into different sections to obtain a segmented image; and means for calculating a series of intermediate corrected images based on the segmented image utilizing a statistical algorithm which accounts for the polyenergetic source spectrum and which converges to obtain a final corrected image which has significantly reduced beam hardening artifacts.

13. The apparatus as claimed in claim 12 wherein the means for calculating includes means for calculating a gradient of a cost function having an argument and means for utilizing the gradient to minimize the cost function with respect to its argument.

14. The apparatus as claimed in claim 13 wherein the means for calculating the gradient includes means for back projecting.

15. The apparatus as claimed in claim 13 wherein the means for calculating the gradient includes means for calculating thicknesses of the components.

16. The apparatus as claimed in claim 15 wherein the means for calculating thicknesses includes means for reprojecting the segmented image.

17. The apparatus as claimed in claim 15 wherein the means for calculating the gradient includes means for calculating means of data along paths and gradients based on the thicknesses of the components.

18. The apparatus as claimed in claim 13 wherein the argument is density of the materials at each image voxel.

19. The apparatus as claimed in claim 12 wherein the means for calculating the gradient includes means for utilizing ordered subsets to accelerate convergence of the algorithm.

20. The apparatus as claimed in claim 13 wherein the cost function has a regularizing penalty term.

* * * * *